(12) United States Patent
Gordon et al.

(10) Patent No.: US 7,956,195 B2
(45) Date of Patent: Jun. 7, 2011

(54) PROCESS FOR THE PREPARATION AND ISOLATION OF THE INDIVIDUAL STEREOISOMERS OF 1-AMINO, 3-SUBSTITUTED PHENYLCYCLOPENTANE-CARBOXYLATES

(75) Inventors: Thomas D. Gordon, Medway, MA (US); Grier A. Wallace, Sterling, MA (US); Martin E. Hayes, Lowell, MA (US); Kirill A. Lukin, Vernon Hills, IL (US); Lei Wang, Acton, MA (US); Dilinie P. Fernando, Groton, CT (US)

(73) Assignee: Abbott Laboratories, Abbott Park, IL (US)

(*) Notice: Subject to any disclaimer, the term of this patent is extended or adjusted under 35 U.S.C. 154(b) by 278 days.

(21) Appl. No.: 12/004,582

(22) Filed: Dec. 21, 2007

(65) Prior Publication Data

US 2008/0255367 A1    Oct. 16, 2008

Related U.S. Application Data

(60) Provisional application No. 60/876,251, filed on Dec. 21, 2006.

(51) Int. Cl.
*C07D 487/00* (2006.01)
*C07D 233/72* (2006.01)
*C07D 235/02* (2006.01)
*C07C 229/48* (2006.01)

(52) U.S. Cl. .................... 548/301.4; 560/43; 562/433

(58) Field of Classification Search .............. 548/301.4; 560/43; 562/433
See application file for complete search history.

(56) References Cited

U.S. PATENT DOCUMENTS

| | | | |
|---|---|---|---|
| 4,841,079 A | 6/1989 | Urban | |
| 2002/0052370 A1* | 5/2002 | Barber et al. | 514/237.5 |
| 2005/0197334 A1 | 9/2005 | Wang et al. | |
| 2005/0250798 A1 | 11/2005 | Dollings et al. | |
| 2006/0051846 A1 | 3/2006 | Ohishi et al. | |
| 2006/0246553 A1 | 11/2006 | Suzuki et al. | |
| 2006/0264457 A1 | 11/2006 | Devasthale et al. | |
| 2008/0096874 A1* | 4/2008 | Birch et al. | 514/222.5 |

FOREIGN PATENT DOCUMENTS

| | | | |
|---|---|---|---|
| WO | WO 9307111 A1 * | 4/1993 | |
| WO | WO 93/10092 | 5/1993 | |
| WO | WO 2006064189 A1 * | 6/2006 | |
| WO | WO 2006/088944 | 8/2006 | |
| WO | WO 2007/098474 | 8/2007 | |

OTHER PUBLICATIONS

Li, Zhen, Discovery of Potent 3, 5-Diphenyl-1, 2, 4-oxadiazole Sphingosine-1-phosphate-1 (S1P1), Journal of Medicinal Chemistry, (2005) pp. 6169-6173, vol. 48(20).
Mandala et al., "Alteration of Lymphocyte Trafficking by Sphingosine—1-Phosphate Receptor Agonists", Science, (2002); 296: 346-349.
Jo et al., "S1P1-Selective In Vivo-Active Agonists from High-Throughput Screening: Off-the-Shelf Chemical Probes of Receptor Interactions, Signaling, and Fate". Chemistry & Biology, (2005); 12: 703-715.
Hale et al., "A Rational Utilization of High-Throughput Screening Affords Selective, Orally Bioavailable 1-Benzyl-3-carboxyazetidine Sphingosine-1-phosphate-1 Receptor Agonists". J. Med. Chem. (2004); 47: 6662-6665.
Clemens et al., "Synthesis of benzimidazole based analogues of sphingosine—1-phosphate: discovery of potent, subtype-selective S1P4 receptor agonists". Bioorganic & Medicinal Chemistry Letters, (2004); 14: 4903-4906.
Clemens et al., "Synthesis of *Para*-Alkyl Aryl Amide Analogues of Sphingosine-1-phosphate: Discovery of Potent S1P Receptor Agonists". Bioorganic & Medicinal Chemistry Letters, (2003); 13: 3401-3404.
Clemens et al., "Synthesis of 4(5)-phenylimidazole-based analogues of sphingosine-1-phosphate and FTY720: Discovery of potent S1P1 receptor agonists". Bioorganic & Medicinal Chemistry Letters (2005); 1-5.
Aspinall et al.; "BINAP: An industrial approach to manufacture". Speciality Chemicals Magazine, Jan./Feb. 2005, p. 34-35.
Froestl et al., "Phosphinic Acid Analogues of GABA. 2. Selective, Orally Active GABAb Antagonists". J. Med. Chem. (1995); 38: 3313-3331.
B. W. Gung, et al., "Total synthesis of two novel brominated acetylenic diols (+)-diplyne C and E: stereoselective construction of the (*E*)-1-bromo-1-alkene". Tetrahedron: Asymmetry (2005); 16: 3107-3114.
Grison, et al., "Synthesis of P-chiral enephosphonic acid derivatives". J. Organomet. Chem. (2002); 662: 83-97.
Prashad, "Phosphonate vs. Phosphinate Elimination During Olefination of Aldehydes" Tetrahedron Letters. (1993); 34: 1585-1588.

* cited by examiner

*Primary Examiner* — Jason M Nolan
(74) *Attorney, Agent, or Firm* — Gayle B. O'Brien; Kenneth P. Zwicker

(57) ABSTRACT

The present invention discloses processes for the preparation and isolation of the individual stereoisomers of 1-amino, 3-substituted phenylcyclopentane-carboxylates.

4 Claims, No Drawings

PROCESS FOR THE PREPARATION AND ISOLATION OF THE INDIVIDUAL STEREOISOMERS OF 1-AMINO, 3-SUBSTITUTED PHENYLCYCLOPENTANE-CARBOXYLATES

CROSS REFERENCE TO RELATED APPLICATION

This application claims priority to U.S. Provisional Application Ser. No. 60/876,251 filed on Dec. 21, 2006, the contents of which are incorporated herein.

BACKGROUND

1-Amino, 3-substitutedphenylcyclopentanecarboxylates are important intermediates for the preparation of a useful class of biologically-active molecules. The processes disclosed in the art for the preparation of these compounds do not address the isolation of stereoisomers with enriched diastereomeric and/or enantiomeric excess. As such there is a need for the development of a process that addresses the isolation of material with diastereomeric and enantiomeric enrichment.

In contrast to previously known processes the present invention discloses an effective method for the preparation and isolation of (1R,3R)-methyl 1-amino-3-(4-bromophenyl)cyclopentanecarboxylate, (1R,3S)-methyl 1-amino-3-(4-bromophenyl)cyclopentanecarboxylate, (1S,3S)-methyl 1-amino-3-(4-bromophenyl)cyclopentanecarboxylate, (1S,3R)-methyl 1-amino-3-(4-bromophenyl)cyclopentanecarboxylate, (1R,3R)-1-amino-3-(4-methoxyphenyl)cyclopentanecarboxylate, (1S,3S)-1-amino-3-(4-methoxyphenyl)cyclopentanecarboxylate which is high yielding and provides for enrichment in both diastereomeric and enantiomeric excess.

These compounds are intermediates in the synthesis of other compounds that possess pharmacological activity. In particular, these other compounds include but are not limited to S1P1 agonists such as those described in WO 2007089715 A2, WO 2006088944 A1 and other publications. S1P1 agonists are useful, e.g., in the treatment of inflammatory diseases and conditions, and in the treatment of other diseases and conditions.

SUMMARY OF THE INVENTION

The present invention relates to the efficient and effective synthesis and isolation of (1R,3R)-methyl 1-amino-3-(4-bromophenyl)cyclopentanecarboxylate, (1R,3S)-methyl 1-amino-3-(4-bromophenyl)cyclopentanecarboxylate, (1S,3S)-methyl 1-amino-3-(4-bromophenyl)cyclopentanecarboxylate, (1S,3R)-methyl 1-amino-3-(4-bromophenyl)cyclopentanecarboxylate, (1R,3R)-1-amino-3-(4-methoxyphenyl)cyclopentanecarboxylate, (1S,3S)-1-amino-3-(4-methoxyphenyl)cyclopentanecarboxylate with greater than 90% de and ee.

In a first embodiment the invention provides a process for the preparation of the mixture of a compound of Formulas 2a and 2b

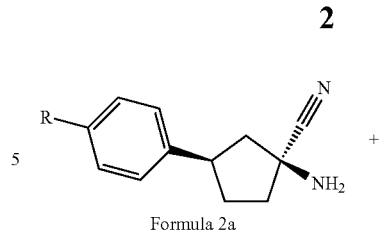

Formula 2a

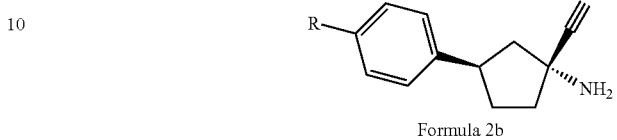

Formula 2b comprising the steps of reacting a compound of Formula 1

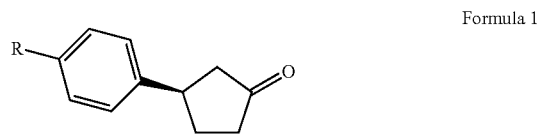

Formula 1 with ammonia and a cyanide salt until the reaction is substantially complete to form the mixture of a compound of Formulas 2a and 2b

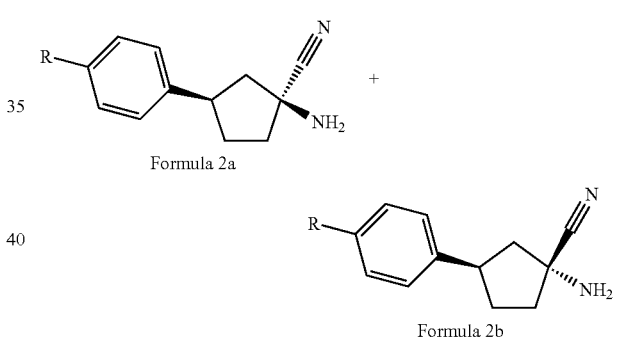

Formula 2a

Formula 2b wherein R is Br or methoxy.

In a second embodiment, the invention provides a process for isolating the compound of Formula 2b

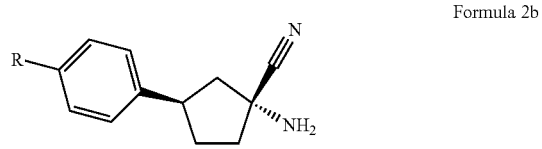

Formula 2b wherein R is Br or methoxy, comprising the steps of forming a salt with L-tartaric acid and separating the diastereomeric salt mixture based on differential solubility in a solvent.

In a third embodiment, the invention provides a process for the preparation of a compound of Formula 3 comprising the steps of reacting a compound of Formula 2b

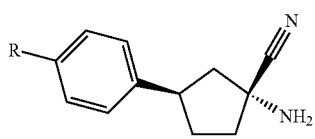

Formula 2b with aqueous HCl and dioxane until the reaction is substantially complete to isolate a compound of Formula 3

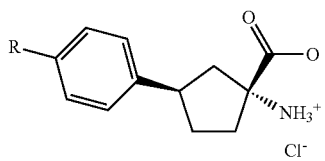

Formula 3 wherein R is Br or methoxy.

In a fourth embodiment, the invention provides a process for preparing a compound of Formula 4

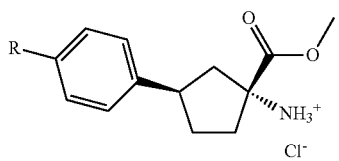

Formula 4 comprising the steps of reacting a compound of Formula 3

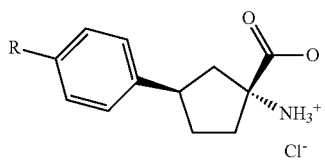

Formula 3 with methanol and thionyl chloride until the reaction is substantially complete to form a compound of Formula 4

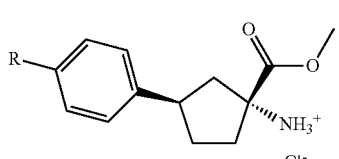

Formula 4 wherein R is Br or methoxy.

In a fifth embodiment, the invention provides a process for preparing a compound of Formula 5

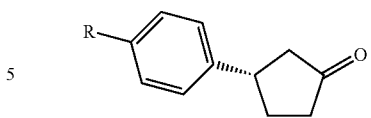

Formula 5 comprising the steps of reacting a substituted arylboronic acid and a rhodium catalyst with (R)- or (S)-BINAP in an organic solvent, water that is degassed with nitrogen and adding a cycloalkenone of the formula

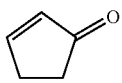

until the reaction is substantially complete to form a compound of Formula 5

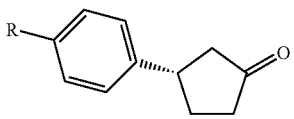

Formula 5 wherein R is Br or methoxy.

In a sixth embodiment, the invention provides a process for the preparation of a mixture of compounds of Formula 6a and Formula 6b

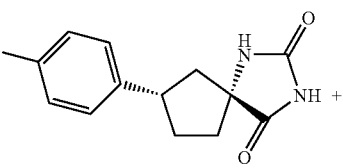

Formula 6a

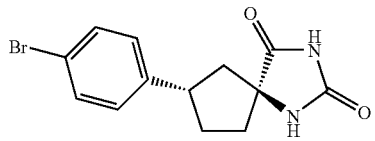

Formula 6b comprising the steps of reacting a mixture of ammonium carbonate and a cyanide salt in water with a compound of Formula 5

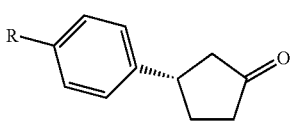

Formula 5 wherein R is Br, until the reaction is substantially complete to give a mixture of compound of Formula 6a and Formula 6b

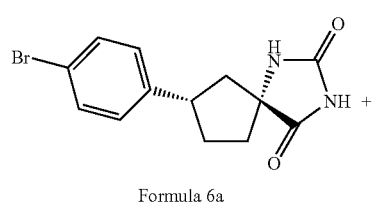

Formula 6a

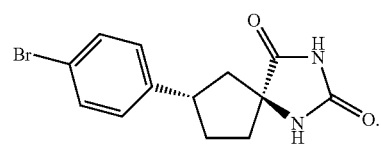

Formula 6b

In a seventh embodiment, the invention provides a process for the preparation of a mixture of compounds of Formula 7a and Formula 7b

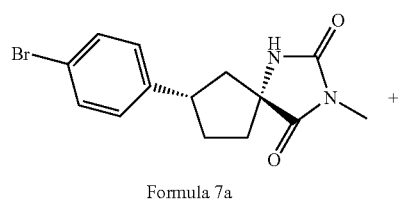

Formula 7a

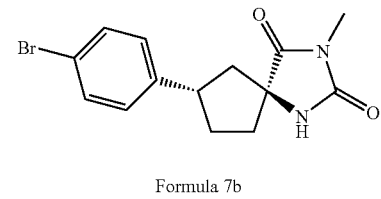

Formula 7b comprising the steps of reacting the mixture of compounds of Formula 6a and Formula 6b

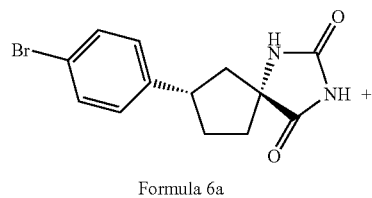

Formula 6a

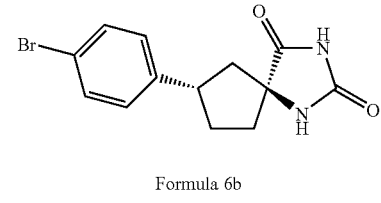

Formula 6b with potassium carbonate and an alkylating agent until the reaction is substantially complete to give a mixture of compounds of Formula 7a and Formula 7b

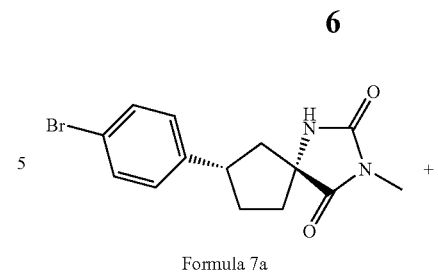

Formula 7a

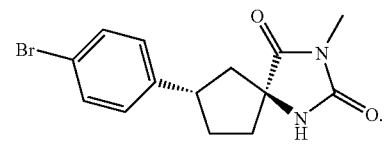

Formula 7b

In an eighth embodiment, the invention provides a process for isolating a compound of Formula 8

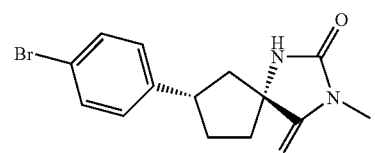

Formula 8 comprising the steps of dissolving the mixture of compounds of Formula 7a and Formula 7b Formula 7a Formula 7b in hot acetonitrile and then cooling the solution until the reaction is substantially complete to give a compound of Formula 8

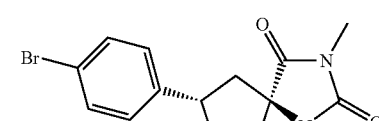

Formula 8

In a ninth embodiment, the invention provides a process for the preparation of a compound of Formula 9

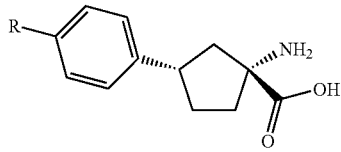
Formula 9 comprising the steps of hydrolizing Formula 8

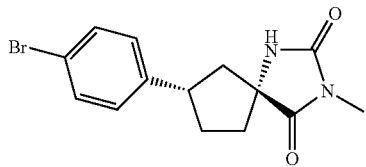
Formula 8 with an aqueous base until the reaction is substantially complete to give a compound of Formula 9

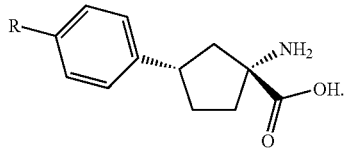
Formula 9

In a tenth embodiment, the invention provides a process for preparing a mixture of compounds of Formula 10a and Formula 10b

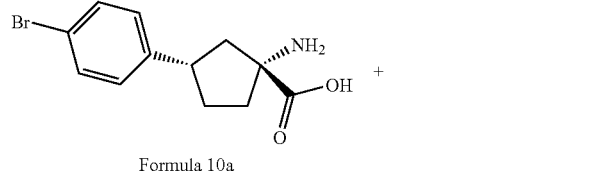
Formula 10a

Formula 10b comprising treating the mixture of compounds of Formula 6a and 6b

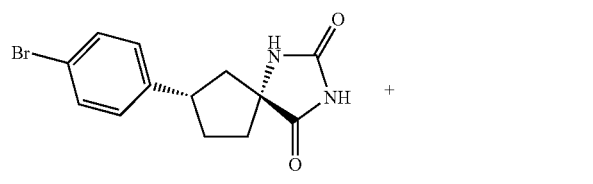
Formula 6a

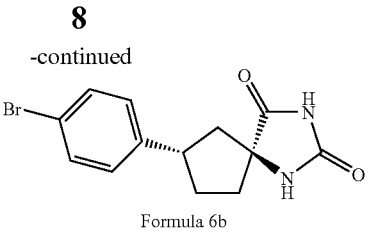
Formula 6b with an inorganic base until the reaction is substantially complete to form a mixture of compounds of Formula 10a and 10b

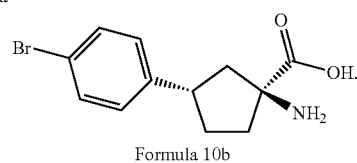
Formula 10a

Formula 10b

In an eleventh embodiment, the invention provides a process for preparing a mixture of compounds of Formula 11a and Formula 11b

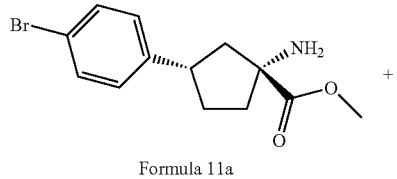
Formula 11a

Formula 11b comprising reacting the mixture of compounds of Formula 10a and Formula 10b

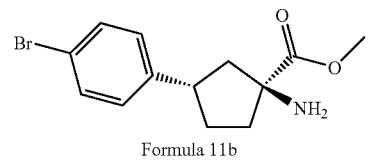
Formula 10a

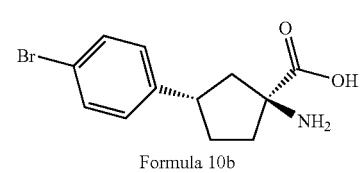
Formula 10b with thionyl chloride and methanol until the reaction is substantially complete to form a mixture of compounds of Formula 11a and Formula 11b

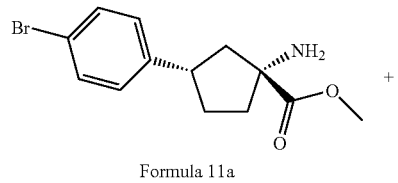

Formula 11a

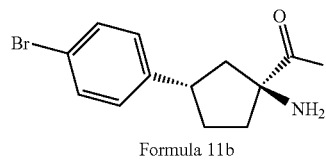

Formula 11b

In a twelfth embodiment, the invention provides a process of isolating a compound of Formula 11a Formula 11a

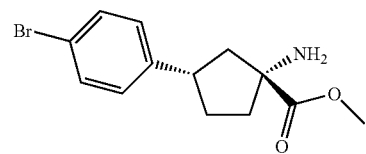

comprising the step of filtering the mixture of compounds of Formula 11a and Formula 11b

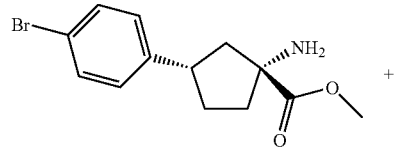

Formula 11a

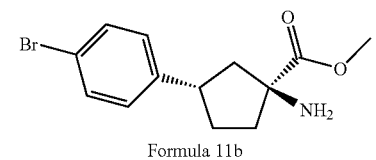

Formula 11b to isolate a compound of Formula 11a

Formula 11a

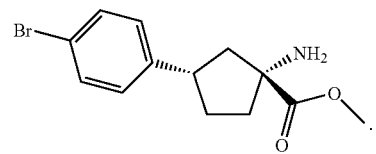

DETAILED DESCRIPTION

| ABBREVIATIONS | |
|---|---|
| ACN | Acetonitrile |
| de | diastereomeric excess |
| DIEA | N,N-Diisopropylethylamine |
| DMA | N,N-Dimethylacetamide |
| DMF | N,N-Dimethylformamide |
| DMSO | Dimethyl sulfoxide |
| ee | enantiomeric excess |
| EtOAc | Ethyl acetate |
| HPLC | High Performance Liquid Chromatography |
| LiOH | Lithium hydroxide |
| MeOH | Methanol |
| $MgSO_4$ | Magnesium sulfate |
| $NaHCO_3$ | Sodium bicarbonate |
| NaOH | Sodium hydroxide |
| Rh | Rhodium |
| $R_t$ | Retention time |
| (R)-BINAP | (R)-(-)-2,2'-Bis(diphenylphosphino)-1,1'-binaphthalene |
| (S)-BINAP | (S)-(-)-2,2'-Bis(diphenylphosphino)-1,1'-binaphthalene |
| TLC | Thin layer chromatography |

Analytical Methods

Analytical data is defined either within the general procedures or in the tables of examples. Unless otherwise stated, all $^1H$ or $^{13}C$ NMR data were collected on a Varian Mercury Plus 400 MHz or a Bruker DRX 400 MHz instrument; chemical shifts are quoted in parts per million (ppm). High-pressure liquid chromatography (HPLC) analytical data are either detailed within the experimental or referenced to the table of HPLC conditions, using the lower case method letter, in Table 1.

TABLE 1

| | List of HPLC methods |
|---|---|
| | HPLC Conditions Unless indicated otherwise mobile phase A was 10 mM ammonium acetate, mobile phase B was |
| Method | HPLC grade acetonitrile. |
| a | 5-95% B over 3.7 min with a hold at 95% B for 1 min (1.3 mL/min flow rate). 4.6 × 50 mm Waters Zorbaz XDB C18 column (5 μm particles). Detection methods are diode array (DAD) and evaporative light scattering (ELSD) detection as well as pos/neg electrospray ionization. |
| b | 98% heptane:2% isopropanol:0.006% diethylamine (flow rate of 0.8 mL/min), column temperature of 20 C., injection volume of 10 μL on a Daicel ChiralPak AD-H 250 mm × 4.6 mm. UV detection at 222 nm. |

General Synthetic Schemes

The general synthetic schemes that were utilized to construct the majority of compounds disclosed in this application are describe below (Schemes 1-3)

Scheme 1. Route to (1R,3R)-1-amino-3-(4-bromopphenyl) cyclopentanecarboxylate via the α-aminonitrile The process for the synthesis and isolation of (1R,3R)-methyl 1-amino-3-(4-bromophenyl)cyclopentanecarboxylate is shown in scheme 1. One skilled in the art should recognize that this process could also be applied to the synthesis of (1S,3S)-methyl 1-amino-3-(4-bromophenyl)cyclopentanecarboxylate.

Scheme 1

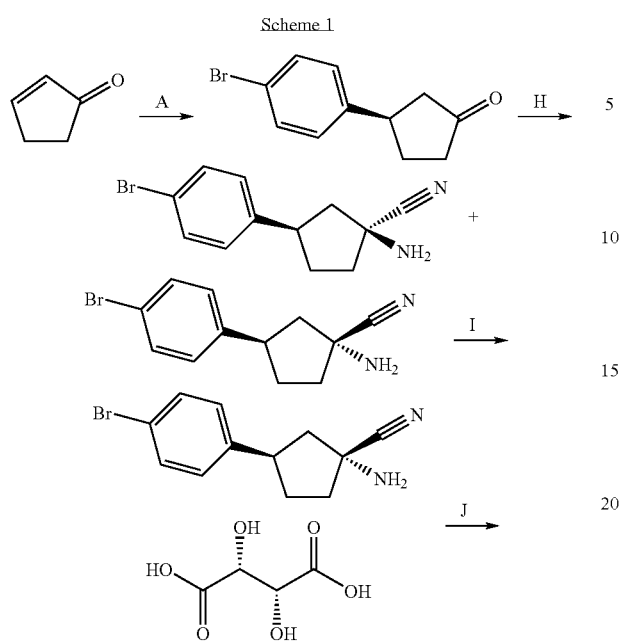

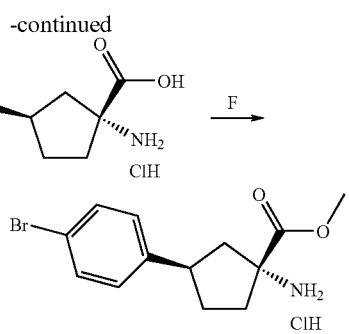

Scheme 2. Route to (1R,3R)-1-amino-3-(4-bromophenyl)cyclopentanecarboxylate, (1R,3S)-1-amino-3-(4-bromopphenyl)cyclopentanecarboxylate, (1S,3R)-1-amino-3-(4-bromopphenyl)cyclopentanecarboxylate and (1S,3S)-1-amino-3-(4-bromopphenyl)cyclopentanecarboxylate via the corresponding hydantoins.

The process for the synthesis and isolation of (1R,3S)-methyl 1-amino-3-(4-bromophenyl)cyclopentanecarboxylate is shown in scheme 2. One skilled in the art should recognize that this process could also be applied to the synthesis of (1S,3R)-methyl 1-amino-3-(4-bromophenyl)cyclopentanecarboxylate.

Scheme 2

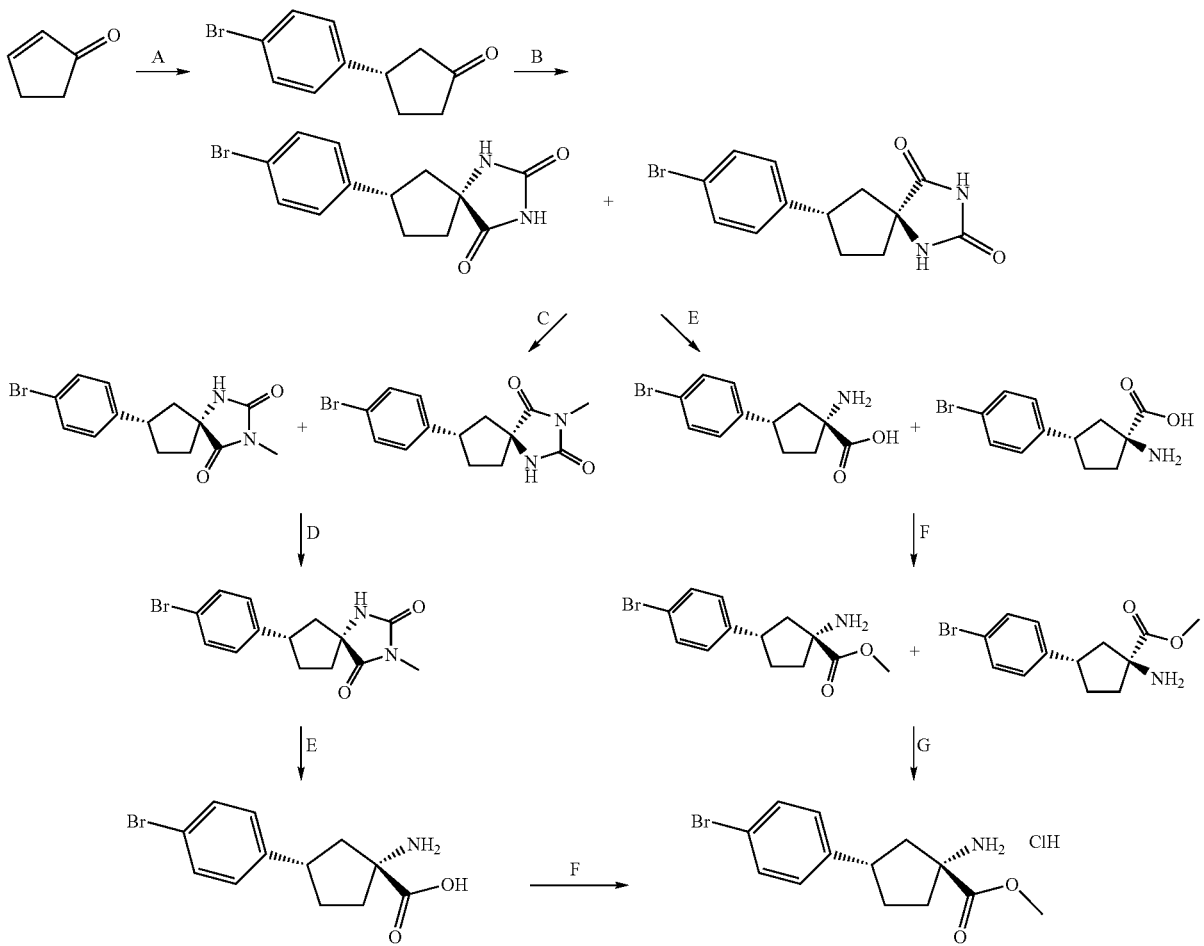

Scheme 3. Route to (1R,3R)-1-amino-3-(4-methoxyphenyl)cyclopentanecarboxylate via the α-aminonitrile.

The process for the synthesis and isolation of (1R,3R)-1-amino-3-(4-methoxyphenyl)cyclopentanecarboxylate is shown in scheme 3. One skilled in the art should recognize that this process could also be applied to the synthesis of (1S,3S)-methyl 1-amino-3-(4-bromophenyl)cyclopentanecarboxylate.

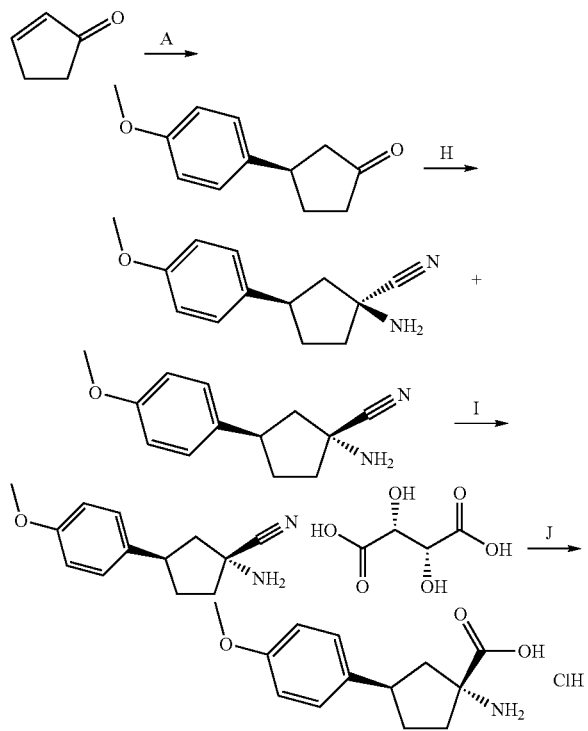

List of General Procedures

General Procedure A: Micheal addition to an alpha-beta unsaturated ketone.

General Procedure B: Formation of a hydantoin from a ketone.

General Procedure C: Formation of an N-alkylated hydantoin.

General Procedure D: Resolution of an N-methyl hydantoin

General Procedure E: Hydrolysis of a hydantoin to the corresponding amino acid.

General Procedure F: Formation of an ester from an acid.

General Procedure G: Resolution of an amino-ester.

General Procedure H: Formation of an α-amino nitrile

General Procedure I: Resolution of α-amino nitrites

General Procedure J: Hydrolysis of an α-amino nitrile

Example of Use of General Procedures

The general procedure letter codes constitute a synthetic route to the final product. A worked example of how the route is determined is given below using Example ## as a non-limiting illustration. The synthesis of the example below was completed using general procedure F as detailed in the General Procedures, i.e.,

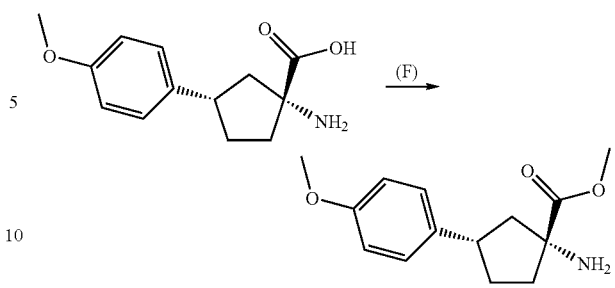

The starting material was prepared using the route (A, H, I, J) (as detailed in the General Procedures). This translates into the following sequence, where the carboxylic acid starting material used in general procedure F is the product of following the procedures A, H, I and J, in the given order.

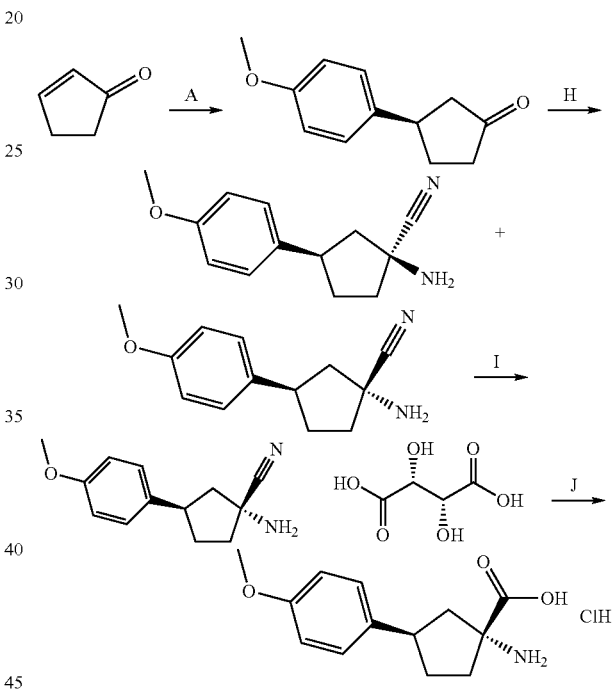

General Procedures

The following describe the synthetic methods illustrated by the foregoing General Procedures schemes and are followed by an example of a compound that was synthesized by the General Procedure. None of the specific conditions and reagents noted in the following are to be construed as limiting the scope of the instant invention and are provided for illustrative purposes only.

General Procedure A: Michael Addition to an Alpha-Beta Unsaturated Ketone

A solution of substituted arylboronic acid (1-3 equivalents, preferably 1.5 equivalents) and a rhodium catalyst (such as Rh(NBD)$_2$ BF$_4$, hydroxy[(S)-BINAP]rhodium(I) dimer, Rh(acac)(C$_2$H$_4$)$_2$/(R)-BINAP, or acetylacetonatobis(ethylene)rhodium(I) with (R)- or (S)-BINAP, preferably Rh(NBD)$_2$ BF$_4$ with (S)-BINAP for (S)-product, Rh(NBD)$_2$/BF$_4$ with (R)-BINAP for (R)-product) (1-5 mol %, preferably 1.25 mol %) in an organic solvent (such as tetrahydrofuran, or dioxane, preferably dioxane) and water is degassed with nitrogen. A cycloalkanone is added to the mixture. The reaction is stirred at about 20-100° C. (preferably about 25° C.) for a period of 1-24 hours (preferably about 16 hours) under inert atmosphere with or without the addition of an organic base (preferably triethylamine). The reaction mixture is concentrated under reduced pressure and the crude product is purified via flash chromatography.

Exemplification of General Procedure A

Preparation of (S)-3-(4-bromo-phenyl)-cyclopentanone

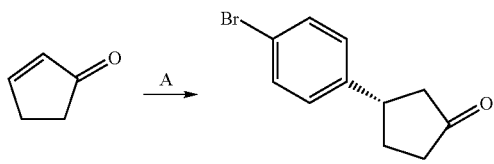

Rh(NBD)₂ BF₄ (22 mg) and S-BINAP (40 mg) are mixed together in degassed 1,4-dioxane (3 mL). The mixture is stirred for 2 h at room temperature to give an orange slurry. In a separate flask, 4-bromophenylboronic acid (1 g, 1.5 eq) is dissolved in dioxane (5.6 mL) and water (1.4 mL) at room temperature, and then transferred into the flask containing the catalyst. The resulting suspension is degassed with nitrogen and 2-cyclopenten-1-one (0.273 g, 1 equivalent) and triethylamine (0.336 g, 1 equivalent) are added. The red-orange clear solution is stirred overnight at room temperature. The reaction is separated between ethyl acetate and water, and the organic layer is washed once with 5% NaCl (aqueous), then concentrated. The crude product is further purified on silica gel column using 20% ethyl acetate in heptanes.

Alternatively, a 3 L three-necked round-bottomed flask equipped with a temperature probe and a nitrogen bubbler was charged with 4-bromophenylboronic acid (100 g, 498 mmol) and hydroxy[(S)-BINAP]rhodium(I) dimer (6.20 g, 4.17 mmol) in dioxane (1667 mL) and water (167 mL) at room temperature. The resulting suspension was degassed with nitrogen and 2-cyclopenten-1-one (27.8 mL, 332 mmol) was added in one portion. The mixture was further degassed for 5 minutes and heated at 35° C. for about 16 hours. The reaction mixture was cooled to room temperature and concentrated. The brown residue was treated with EtOAc (500 mL) and filtered. The filtrate was washed with a saturated solution of NaHCO₃ (500 mL) and brine (500 mL), dried over MgSO₄, filtered, and concentrated to afford a dark brown solid. The crude reaction product was purified by silica gel chromatography (1:9 EtOAc:heptane as eluant). Fractions containing product were combined and concentrated to afford (S)-3-(4-bromo-phenyl)-cyclopentanone (70.4 g, 89%, 95% ee as determined by chiral HPLC) as an ivory solid.

LCMS (Table 1, Method a) $R_f$=2.81 min; no characteristic mass detected; ¹H NMR (400 MHz, DMSO-d₆) δ7.47 (d, 2H), 7.27 (d, 2H), 3.35 (m, 1H), 2.55 (m, 1H), 2.25 (m, 4H), 1.85 (m, 1H)

Alternatively, the boronate can be formed in situ and used in the rhodium catalyzed addition to an enone as follows. A 250 mL round-bottomed flask equipped with a rubber septum and nitrogen inlet needle is charged with 1-bromo-4-octylbenzene (5.77 g, 21.43 mmol) in Et₂O (10.7 ml) at room temperature. The resulting solution is cooled to 0° C. After 5 min BuLi (8.21 ml, 21.43 mmol) solution is added dropwise via syringe over 20 min. The reaction mixture was allowed to stir at 0° C. for 30 min. The resulting solution is then cooled to −78° C. After 10 min trimethyl borate (2.395 ml, 21.43 mmol) is added dropwise via syringe over 5 min. The reaction mixture is allowed to stir at −78° C. for 30 min. The reaction mixture is treated with 20 mL of saturated NH₄Cl and 50 ml of toluene. The aqueous phase is separated and extracted with two 50-mL portions of toluene. The organic phases are combined and concentrated. The residue is further diluted with toluene and concentrated to remove water and then dried in vacuo. The resulting white pasty solid is used directly in the next transformation. The crude borate is transferred to a 200 ml round-bottomed flask equipped with a reflux condenser outfitted with a nitrogen inlet adapter while acetylacetonatobis(ethylene)rhodium(I) (0.166 g, 0.643 mmol) and (R)-BINAP enantiomer (0.480 g, 0.772 mmol) are added in one portion each. The flask is evacuated and filled with nitrogen (three cycles to remove oxygen). To the solid is added dioxane (40 ml), cyclopent-2-enone (1.796 ml, 21.43 mmol), and water (4 ml) each dropwise via syringe. The resulting suspension is heated at 100° C. for 16 h. The resulting orange/brown solution is allowed to cool to room temperature. The orange/brown solution is concentrated and the brown residue is taken up in ether and washed with 1N HCl solution. A tan emulsion forms. The emulsified mixture is separated and extracted with EtOAc. The aqueous phases are also extracted with EtOAc. The combined organic phases are washed with 10% NaOH and Brine, then concentrated to afford a brown oil. The crude sample is purified via chromatography on silica gel to afforded 1258 mg of colorless oil.

General Procedure B: Formation of a Hydantoin from a Ketone

To a mixture of ammonium carbonate (1-10 equivalents, preferably 4.5 equivalents) and a cyanide salt (such as potassium cyanide, or sodium cyanide) (1-3 equivalents, preferably 1.1 equivalents) in water is added a ketone (1 equivalent). The reaction mixture is heated to reflux for a period of 2-40 hours (preferably 16 hours). The reaction mixture is cooled to room temperature and the solid is collected by filtration, and washed with water to give the crude product that can be purified by trituration with ether.

Exemplification of General Procedure B

Preparation of (S)-7-(4-bromo-phenyl)-1,3-diazaspiro[4.4]nonane-2,4-dione

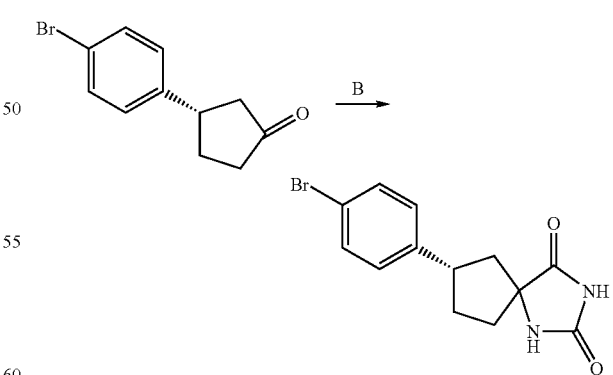

To a round bottom flask charged with ammonium carbonate (268 g, 2.79 mol) and potassium cyanide (44.4 g, 0.681 mol) was added water (1500 mL, 82 mol). The mixture was heated at 80° C. and a solution of (S)-3-(4-bromo-phenyl)-cyclopentanone (148.09 g, 0.62 mol) in ethanol (1500 mL, 25 mol) was added. The reaction mixture was heated to reflux overnight. The reaction mixture was cooled to room temperature. The crude reaction mixture was filtered and washed with water. The solid was triturated with ether (1.5 L), filtered, washed with ether and dried under vacuum to yield (S)-7-(4-bromo-phenyl)-1,3-diaza-spiro[4.4]nonane-2,4-dione (181.29 g, 95%) as a 1:1 mixture of diastereomers.

LCMS (Table 1, Method a) $R_t$=2.24 min; m/z: 307 (M−H)⁻; ¹H NMR (400 MHz, DMSO-$d_6$) δ 10.61 (s, 1H), 8.29 (s, 1H), 8.24 (s, 1H), 7.49 (d, 2H), 7.27 (d, 1H), 7.24 (d, 1H), 3.14-3.35 (m, 1H), 2.45 (dd, 0.5H), 1.68-2.27 (m, 5.5H)

General Procedure C: Formation of an N-Alkylated Hydantoin

To a flask containing the hydantoin (1 equivalent) is added a base (such as potassium carbonate, or sodium carbonate) (1-3 equivalents, preferably 1.5 equivalents) and an organic solvent such as DMF, or DMA (preferably DMF). The mixture is stirred at room temperature for a period of 10-30 minutes (preferably about 15 minutes), then methyl iodide (1-2 equivalents, preferably 1.1 equivalents) is added. The reaction is stirred at room temperature for a period of 24-72 hours (preferably about 48 hours). The reaction mixture is concentrated, cooled down in an ice-water bath, and water is added. The precipitate is collected by filtration to give the crude product. The two stereoisomers can be separated by crystallization.

Exemplification of General Procedure C

Preparation of (5R,7S)-7-(4-bromo-phenyl)-3-methyl-1,3-diaza-spiro[4.4]nonane-2,4-dione

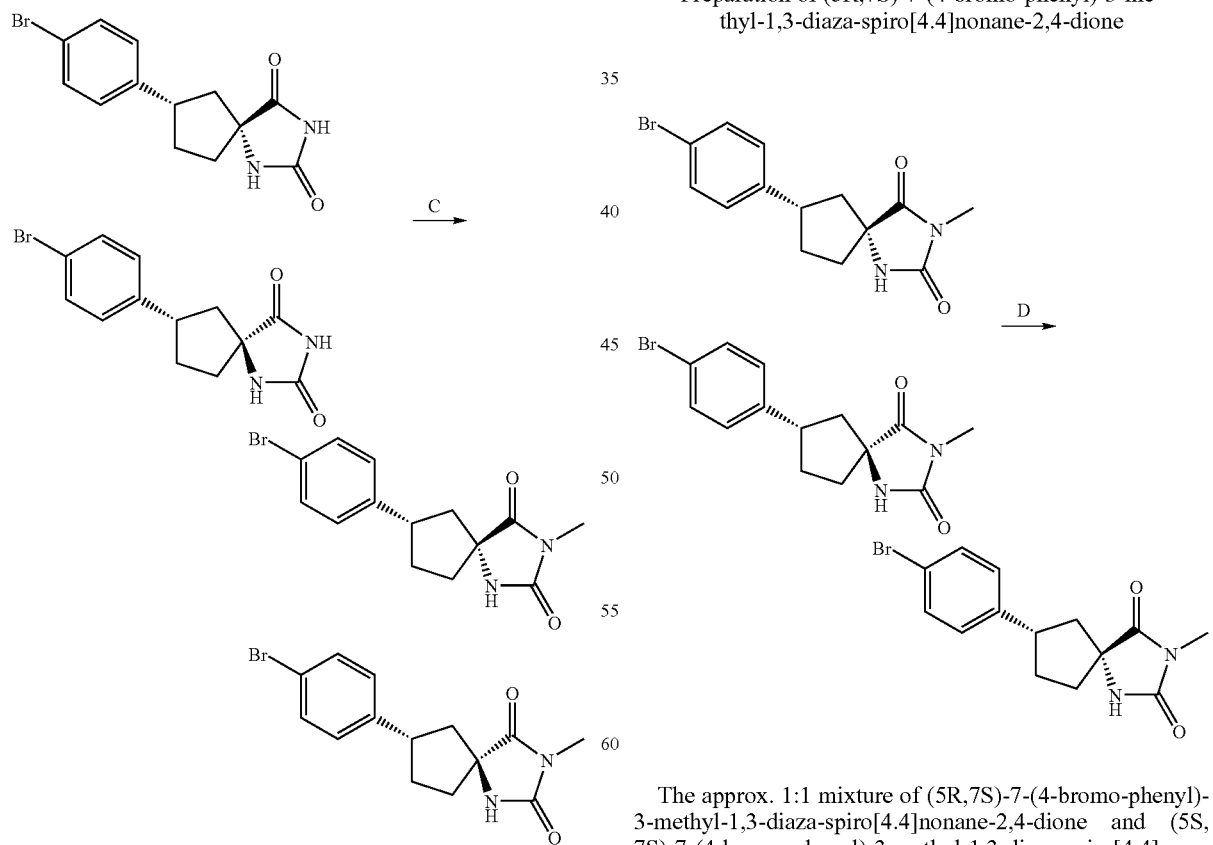

To the flask containing (S)-7-(4-Bromo-phenyl)-1,3-diaza-spiro[4.4]nonane-2,4-dione (1:1 mixture of diastereomers, 180.3 g, 0.583 mol) was added potassium carbonate (120.9 g, 0.875 mol) followed by DMF (1 L). After stirring for 15 minutes at room temperature, methyl iodide (39.9 mL, 0.642 mol) was added in one portion. The reaction was stirred at room temperature over two days. The reaction mixture was partially concentrated in vacuo at 25° C., removing approximately 400 mL of DMF and excess methyl iodide. The crude mixture was cooled in an ice water bath and water (2 L) was added. After stirring for 1 hour the resulting white precipitate was filtered and rinsed with water (1 L). The filter cake was dried on house vacuum overnight to give 220 g crude (S)-7-(4-Bromo-phenyl)-3-methyl-1,3-diaza-spiro[4.4]nonane-2,4-dioneas as a mixture of diastereomers.

LCMS (Table 1, Method a) $R_t$=2.50 min; m/z: 321 (M−H)⁻; ¹H NMR (400 MHz, DMSO-$d_6$) δ 8.56 (s, 1H), 7.50 (d, 2H, J=8.42 Hz), 7.27 (d, 2H, J=8.53 Hz), 3.16-3.31 (m, 1H), 2.84 (s, 3H), 2.46 (dd, 1H, J=13.62, 8.40 Hz,), 2.02-2.18 (m, 2H), 1.72-1.95 (m, 3H)

General Procedure D: Resolution of an N-methyl hydantoin

A mixture of N-methyl hydantoins is suspended in an organic solvent (preferably actonitrile) at concentration of approximately 1 g per about 1 to about 100 mL (preferably 1 g per about 23 mL). The slurry is heated to about 50 to about 100° C. with stirring until the solid dissolves. If the solution is not homogeneous the solution is filtered hot. The homogeneous solution is then allowed to cool and aged until significant amounts of solid are present. The solid is collected by filtration.

Exemplification of General Procedure D

Preparation of (5R,7S)-7-(4-bromo-phenyl)-3-methyl-1,3-diaza-spiro[4.4]nonane-2,4-dione

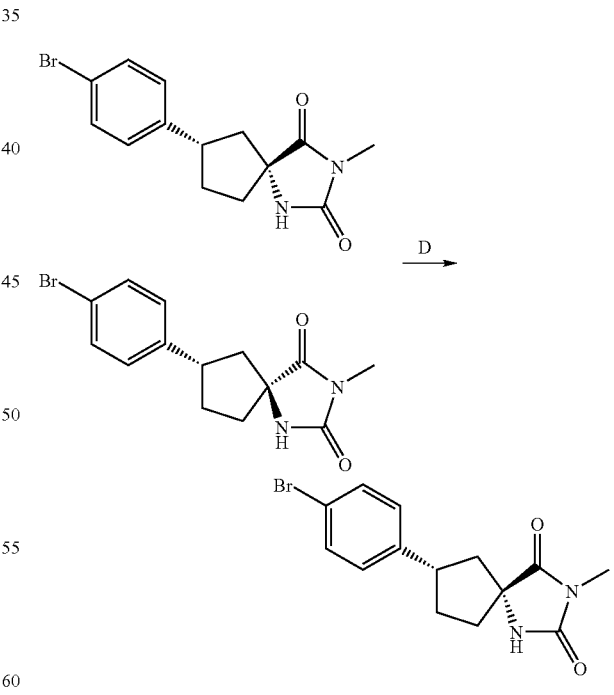

The approx. 1:1 mixture of (5R,7S)-7-(4-bromo-phenyl)-3-methyl-1,3-diaza-spiro[4.4]nonane-2,4-dione and (5S,7S)-7-(4-bromo-phenyl)-3-methyl-1,3-diaza-spiro[4.4]nonane-2,4-dione (110 g) was suspended in ACN (2.5 L) and heated to 70° C. until near complete dissolution occurred. The material was filtered rapidly at 70° C. and rinsed with 70° C.

ACN (2×500 mL). The combined filtrates (3.5 L total vol.) were reheated to 65° C. with stirring. After a clear solution was obtained the mixture was allowed to cool slowly to 50° C. at which point material began to come out of solution. The solution was allowed to slowly cool to 30° C. with stirring (100 rpm). After aging for 2 hours the solution was filtered and the solid was dried at 65° C. under house vacuum for three hours to give (5R,7S)-7-(4-bromo-phenyl)-3-methyl-1,3-diaza-spiro[4.4]nonane-2,4-dione (22.2 g, 12%).

LCMS (Table 1, Method a) $R_t$=2.50 min; m/z: 321 (M−H)−; $^1$H NMR (400 MHz, DMSO-$d_6$) δ 8.56 (s, 1H), 7.50 (d, 2H, J=8.42 Hz), 7.27 (d, 2H, J=8.53 Hz), 3.16-3.31 (m, 1H), 2.84 (s, 3H), 2.46 (dd, 1H, J=13.62, 8.40 Hz,), 2.02-2.18 (m, 2H), 1.72-1.95 (m, 3H)

General Procedure E: Hydrolysis of a Hydantoin to the Corresponding Amino Acid

To a suspension of N-alkylated hydantoin (1 equivalent) in a mixture of water and organic solvent (preferably water/dioxane or water/DMSO) is added an inorganic base (such as lithium hydroxide, or sodium hydroxide) (5-15 equivalents, preferably about 8-10 equivalents). The mixture is heated to reflux for a period of 16-48 hours (preferably 24 hours). After cooling to room temperature, the reaction mixture is diluted, acidified, and filtered. The filter cake is washed with a suitable solvent (preferably water, ethyl acetate or methanol), if necessary, slurried in toluene to remove excess water, and dried under vacuum.

Exemplification of General Procedure E

Preparation of (1R,3S)-1-amino-3-(4-bromo-phenyl)-cyclopentanecarboxylic acid

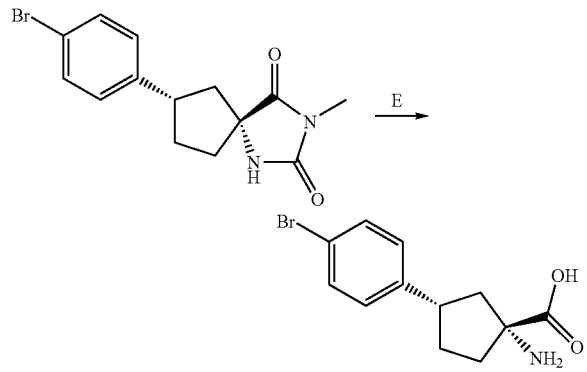

To a slurry of (5R,7S)-7-(4-bromo-phenyl)-3-methyl-1,3-diaza-spiro[4.4]nonane-2,4-dione (79 g, 0.24 mol) in water (1 L) was added 2 M aqueous NaOH (1 L, 2 mol) and dioxane (200 mL). The resulting mixture was heated to reflux for 24 hours. The reaction mixture was cooled to room temperature, diluted with water (2 L) and acidified with concentrated HCl until a precipitate began to form (about pH 7). Acetic acid (about 20 mL) was added, producing a thick precipitate. The white precipitate was collected and washed with water (2×1 L) and EtOAc (1 L). The filter cake was suspended in toluene (1 L) and concentrated in vacuo at 45° C. This process was repeated once more. The white precipitate was dried to a constant weight under vacuum to give (1R,3S)-1-amino-3-(4-bromo-phenyl)-cyclopentanecarboxylic acid (65 g, 95%).

LCMS (Table 1, Method a) $R_t$=1.56 min; m/z: 284/286 (M+H)+; $^1$H NMR (400 MHz, DMSO-$d_6$) δ 7.55 (d, 2H), 7.3 (d, 2H), 3.3 (m, 1H), 2.65 (m, 1H), 2.3 (m, 1H), 2.1-2.2 (m, 2H), 2.0-2.1 (m, 1H), 1.85 (t, 1H)

General Procedure F: Formation of an Ester from an Acid

An acid (1 equivalent) suspended in large excess of methanol is cooled in an ice/water bath and thionyl chloride (5-20 equivalents, preferably 8-12 equivalents) is added dropwise. The resulting mixture is heated to reflux for a period of 2-48 hours (preferably 24-36 hours). The reaction mixture is cooled to room temperature, filtered and concentrated to dryness. The residue is triturated with a suitable solvent (such as EtOAc, or ether) and dried under vacuum to give the desired product.

Exemplification of General Procedure F

Preparation of (1R,3S)-1-amino-3-(4-bromo-phenyl)-cyclopentanecarboxylic acid methyl ester; hydrochloride

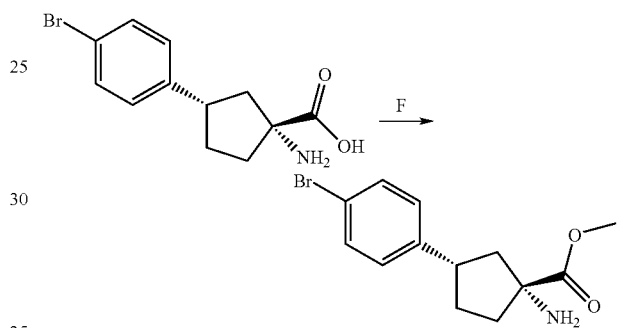

The (1R,3S)-1-amino-3-(4-bromo-phenyl)-cyclopentanecarboxylic acid (79 g, 0.28 mol) suspended in MeOH (1.8 L) was cooled in an ice/water bath and thionyl chloride (178 mL, 2.44 mol) was added dropwise. Following the addition the reaction was heated to reflux. After 2 days the reaction mixture was cooled to room temperature, filtered, and rinsed with MeOH (2×200 mL). The filtrate was concentrated in vacuo to provide a white solid. The white solid was triturated with EtOAc (1 L), collected by filtration, rinsed with EtOAc (2×500 mL), and dried under vacuum to give the (1R,3S)-1-amino-3-(4-bromo-phenyl)-cyclopentanecarboxylic acid methyl ester; hydrochloride as a white solid (79 g, 96%).

LCMS (Table 1, Method a) $R_t$=1.80 min (ELSD); m/z: 198 (M+H)+; $^1$H NMR (400 MHz, DMSO-$d_6$) δ 7.55 (d, 2H), 7.35 (d, 2H), 3.82 (s, 3H), 3.3 (m, 1H), 2.65 (m, 1H), 2.3 (m, 1H), 2.1-2.2 (m, 3H), 1.95-2.05 (t, 1H). Chiral HPLC (Table 1, Method b).

General Procedure G: Resolution of an Amino-Ester.

To a mixture of the amino acids (about 1 equivalent) suspended in large excess of methanol is cooled in an ice/water bath and thionyl chloride (5-20 equivalents, preferably 8-12 equivalents) is added dropwise. The resulting mixture is heated to reflux for a period of 2-48 hours (preferably 24-36 hours). The reaction mixture is cooled to room temperature, concentrated and is suspended in about 5-25 volumes (preferably 15 volumes) of a solution of about 1 to 15% (preferably 5%) water in an organic solvent (preferably DME). The mixture is heated to about 30-100° C. (preferably 50° C.) for about 3 hrs. After cooling to about room temperature the mixture is filtered. The procedure is repeated about 1 to 5 times (preferably 1 time) to provide the desired methyl ester with about >95% ee and about >95% de.

Exemplification of General Procedure G

Isolation of (1R,3S)-methyl 1-amino-3-(4-bromophenyl)cyclopentanecarboxylate hydrochloride

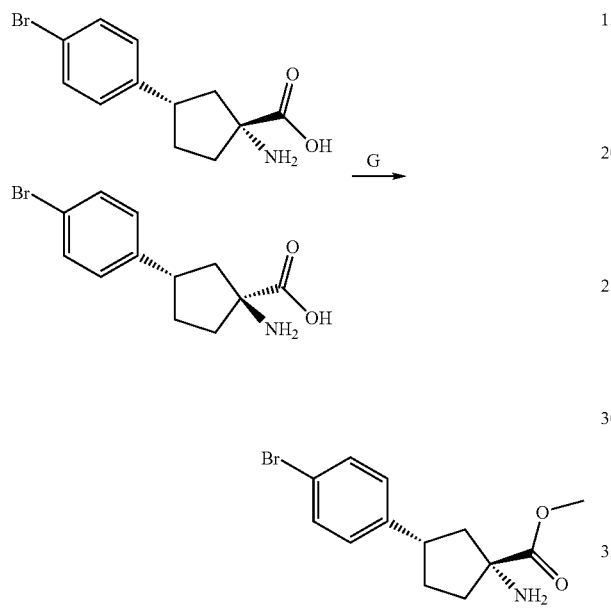

The crude mixture of (1R,3S)-1-amino-3-(4-bromo-phenyl)-cyclopentanecarboxylic acid methyl ester; hydrochloride and (1S,3S)-1-amino-3-(4-bromo-phenyl)-cyclopentanecarboxylic acid methyl ester; hydrochloride (from General Procedure F) (approx. 2.6 mol) was combined with 15 L of aqueous 1,2-DME solution (4.8% water content). The slurry was mixed for 3 h at 50° C., allowed to cool to room temperature and mixed at room temperature for 15 h. The resulting mixture is filtered and dried in vacuo at 60° C. to provide (1R,3S)-methyl 1-amino-3-(4-bromophenyl)cyclopentanecarboxylate hydrochloride hydrate as a white solid (332 g, 36% yield). Chiral HPLC (Table 1, Method b). $R_t$=19.9 min., LCMS (Table 1, Method a) $R_t$=1.80 min (ELSD); m/z: 198 (M+H)⁺.

General Procedure H: Formation of an α-amino nitrile

A solution of a ketone (1 equivalent) in methanolic ammonia is treated with sodium cyanide (1-4 equivalents, preferably about 2 equivalents) and ammonium chloride (1-4 equivalents, preferably about 2 equivalents), and the mixture is allowed to stir at room temperature for 12-72 hours. Solvents are removed under reduced pressure and the residue is treated with an aqueous base such as sodium carbonate or sodium bicarbonate and the aminonitrile is extracted with an organic solvent such as ethyl acetate or methylene chloride and concentrated.

Exemplification of General Procedure H

Exemplification H1

Preparation of (1R,3R)-1-Amino-3-(4-methoxy-phenyl)-cyclopentanecarbonitrile and (1S,3R)-1-Amino-3-(4-methoxy-phenyl)-cyclopentanecarbonitrile

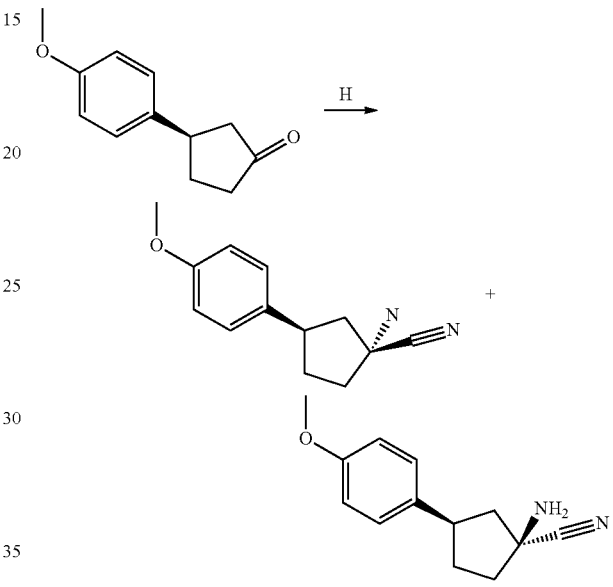

A solution of (R)-3-(4-Methoxy-phenyl)-cyclopentanone (11.0 g, 57.9 mmol) in 7M methanolic ammonia solution (120 ml) was treated with ammonium chloride (6.21 g, 116 mmol) and sodium cyanide (5.68 g, 116 mmol). The reaction was stoppered and stirred at room temperature for 2 days. The reaction was concentrated, treated with saturated NaHCO₃ solution (80 ml) and extracted with CH₂Cl₂ (2×100 ml). The CH₂Cl₂ extracts were washed with water (40 ml), dried (MgSO₄) and concentrated to yield a mixture of (1R,3R)-1-Amino-3-(4-methoxy-phenyl)-cyclopentanecarbonitrile and (1S,3R)-1-Amino-3-(4-methoxy-phenyl)-cyclopentanecarbonitrile as an oil (12.4 g) which was used in the resolution without further purification. LCMS (Table 1, Method a) $R_t$=2.17 min; m/z: 217.1 (M+H)⁺;

Exemplification H2

Preparation of (1R,3R)-1-Amino-3-(4-bromo-phenyl)-cyclopentanecarbonitrile and (1S,3R)-1-Amino-3-(4-bromo-phenyl)-cyclopentanecarbonitrile

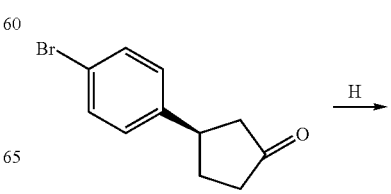

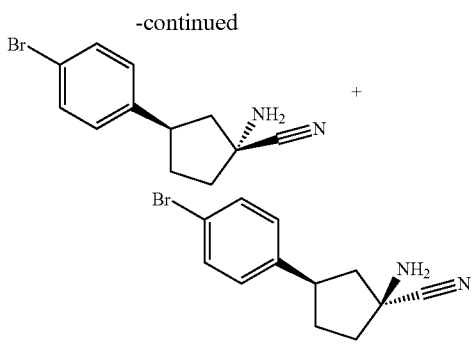

A solution of (R)-3-(4-Bromo-phenyl)-cyclopentanone (21.5 g, 90.0 mmol) in 7M methanolic ammonia solution (220 ml) was treated with ammonium chloride (9.63 g, 180 mmol) and sodium cyanide (8.82 g, 180 mmol). The reaction was stoppered and stirred at room temperature for 3 days. The reaction was concentrated, treated with saturated NaHCO$_3$ solution (400 ml) and extracted with EtOAc (400 ml). The EtOAc layer was washed with saturated NaCl (300 ml) and used in the resolution step without further purification. LCMS (Table 1, Method a) R$_t$=2.61 min; m/z: 265.1/267.1 (M+H)$^+$ General Procedure I: Resolution of α-amino nitriles The crude product from General Procedure H is re-dissolved in a suitable organic solvent such as methanol or ethyl acetate and treated with a methanolic solution of either D-Tartaric acid or L-Tartartic acid. The precipitate is washed with a solvent (water, acetonitrile, methanol, ethanol, acetone, or aqueous mixtures of miscible organic solvents) to remove the more soluble diastereomer.

Exemplification of General Procedure I

Exemplification I1

Preparation of (1R,3R)-1-Amino-3-(4-methoxy-phenyl)-cyclopentanecarbonitrile; compound with (2R,3R)-2,3-dihydroxy-succinic acid

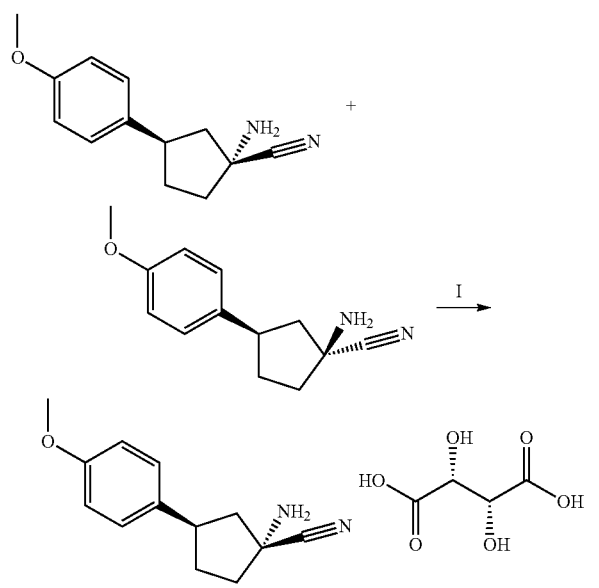

The mixture of (1R,3R)-1-Amino-3-(4-methoxy-phenyl)-cyclopentanecarbonitrile and (1S,3R)-1-Amino-3-(4-methoxy-phenyl)-cyclopentanecarbonitrile (12.4 g), from Exemplification H1, was dissolved in methanol (100 ml) and added to a solution of L-Tartaric acid (8.69 g, 57.9 mmol) in methanol (100 ml). The resulting solid was filtered off and triturated repeatedly with 80 ml portions of methanol until the more soluble isomer was very nearly gone as indicated by HPLC (ThermoQuest 50×4.6 mm, 5 u, Hypercarb column, part # 35005-025). The remaining white solid was dried to yield 6.0 g (28%) of (1R,3R)-1-Amino-3-(4-methoxy-phenyl)-cyclopentanecarbonitrile; compound with (2R,3R)-2,3-dihydroxy-succinic acid. NMR (DMSO-d6) 7.18 (d, 2H), 6.85 (d, 2H), 4.22 (s, 2H), 3.72 (s, 3H), 3.30-3.41 (m, 1H), 2.10-2.30 (m, 3H), 1.8-2.0 (m, 2H), 1.6-1.75 (m, 1H), LCMS (ELSD) no parent ion, R$_t$=2.26 min Exemplification I2

Preparation of (1R,3R)-1-amino-3-(4-bromo-phenyl)-cyclopentanecarbonitrile; 2:1 compound with (2R,3R)-2,3-dihydroxy-succinic acid

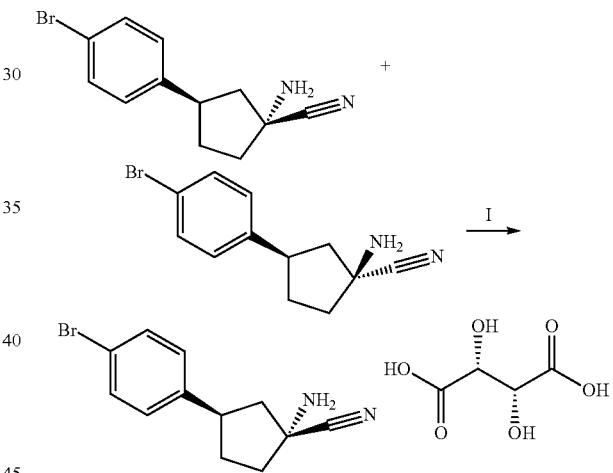

The mixture of (1R,3R)-1-Amino-3-(4-bromo-phenyl)-cyclopentanecarbonitrile and (1S,3R)-1-Amino-3-(4-bromo-phenyl)-cyclopentanecarbonitrile in EtOAc (400 ml) from Exemplification H2, was treated with L-Tartaric acid (13.5 g, 90.0 mmol) and the EtOAc was removed on the roto-vap. The resulting white solid was filtered off and triturated with water (9×250 ml) until the more soluble isomer was very nearly gone as indicated by HPLC (ThermoQuest 50×4.6 mm, 5 u, Hypercarb column, part # 35005-025). The remaining white solid was dried to yield 14.5 g (47%) of crude (1R,3R)-1-Amino-3-(4-bromo-phenyl)-cyclopentanecarbonitrile; 2:1 compound with (2R,3R)-2,3-dihydroxy-succinic acid. NMR (DMSO) 7.45 (d, 2H), 7.23 (d, 2H), 4.01 (s, 1H), 3.30-3.45 (m, 1H), 2.50 (m, 1H), 2.10-2.35 (m, 3H), 1.8-2.0 (m, 2H), 1.6-1.75 (m, 1H).

General Procedure J: Hydrolysis of an α-amino nitrile

The tartrate salt (or bi-tartrate salt) of an α-aminonitrile is heated with a mixture of 6N HCl and dioxane at a concentration of about 0.1-0.2 g/ml. The mixture is heated at reflux for 4-48 hours (preferably about 18 hours), and then allowed to cool to room temperature. The resulting precipitate is filtered off, washed with water and dried.

Exemplification of General Procedure I

Exemplification I1

Preparation of (1R,3R)-1-Amino-3-(4-methoxy-phenyl)-cyclopentanecarboxylic acid; hydrochloride

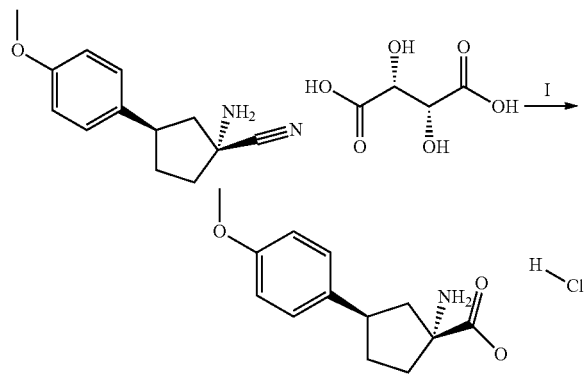

A suspension of (1R,3R)-1-Amino-3-(4-methoxy-phenyl)-cyclopentanecarbonitrile; compound with (2R,3R)-2,3-dihydroxy-succinic acid (5.0 g, 13.66 mmol) in 6N hydrochloric acid (50 ml) and p-dioxane (5 ml) was heated overnight under nitrogen at 100° C. The reaction was cooled on ice and the product was filtered off, washed with water (3×5 ml) and dried to yield 2.72 g (74%), of (1R,3R)-1-Amino-3-(4-methoxy-phenyl)-cyclopentanecarboxylic acid; hydrochloride as a white solid. NMR (DMSO-d6) 13.9 (s(broad), 1H), 8.55 (s(broad), 3H), 7.17 (d, 2H), 6.88 (d, 2H), 3.40-3.52 (m, 1H), 2.28-2.40 (m, 2H), 2.13-2.20 (m, 2H), 1.90-1.99 (m, 1H), 1.74-1.85 (m, 1H). LCMS (ELSD), 236 MH+, $R_t$=1.43 min.

Exemplification I2

Preparation of (1R,3R)-1-Amino-3-(4-bromo-phenyl)-cyclopentanecarboxylic acid; hydrochloride

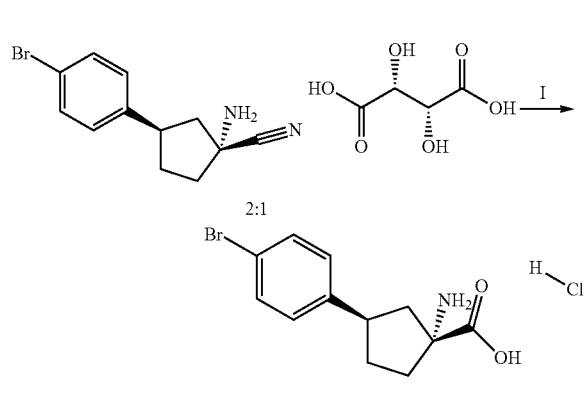

A suspension of (1R,3R)-1-Amino-3-(4-bromo-phenyl)-cyclopentanecarbonitrile; 2:1 compound with (2R,3R)-2,3-dihydroxy-succinic acid (14.4 g, 42.4 mmol) in 6N hydrochloric acid (72 ml) and p-dioxane (72 ml) was heated 24 hours under nitrogen at 100° C. The reaction was cooled to room temperature and the product was filtered off, washed with water (2×25 ml) and dried to yield 7.91 g (58%), of crude (1R,3R)-1-Amino-3-(4-bromo-phenyl)-cyclopentanecarboxylic acid; hydrochloride. Crude product (6.89 g) was further purified by trituration with 3×25 ml of EtOAc then re-dried to yield white solid 6.29 g, (53%). NMR (DMSO) 13.9 (s(broad), 1H), 8.5 g (s(broad), 3H), 7.51 (d, 2H), 7.23 (d, 2H), 3.50 (m, 1H), 2.30-2.42 (m, 2H), 2.10-2.26 (m, 2H), 1.90-2.05 (m, 1H), 1.75-1.88 (m, 1H).

The teachings of all references, including journal articles, patents and published patent applications, are incorporated herein by reference in their entirety.

What is claimed:

1. A process for the preparation of a mixture of compounds of Formula 7a and Formula 7b

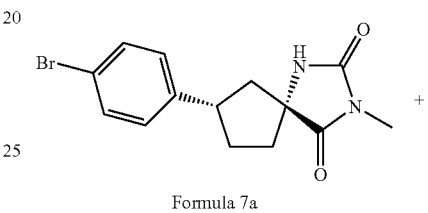

Formula 7a

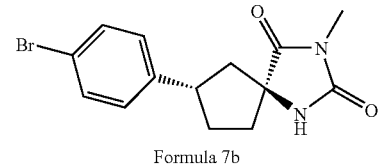

Formula 7b comprising the steps of reacting the mixture of compounds of Formula 6a and Formula 6b

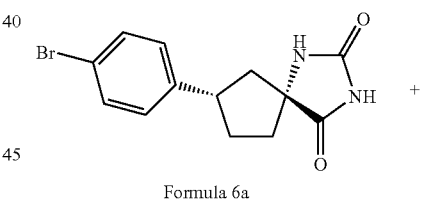

Formula 6a

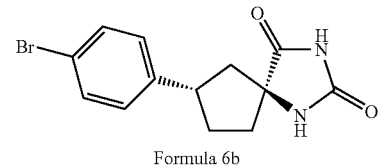

Formula 6b with potassium carbonate and an alkylating agent to give a mixture of compounds of Formula 7a and Formula 7b

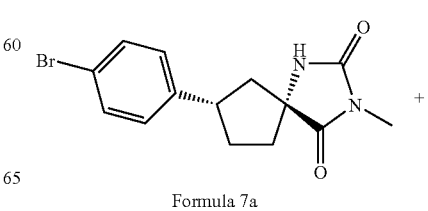

Formula 7a

-continued

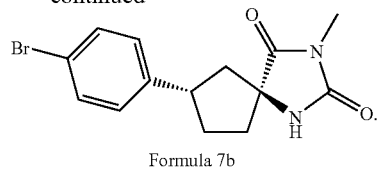

Formula 7b

2. A process for isolating a compound of Formula 8

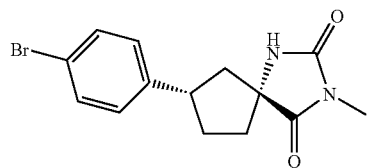

Formula 8 comprising the steps of dissolving the mixture of compounds of Formula 7a and Formula 7b

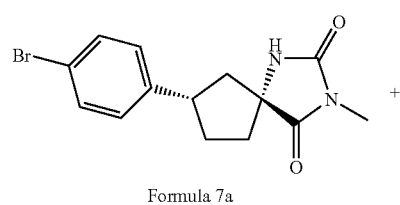

Formula 7a

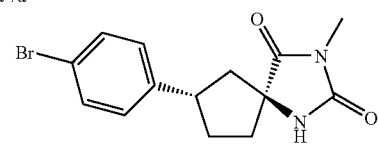

Formula 7b in hot acetonitrile and then cooling the solution to give a compound of Formula 8

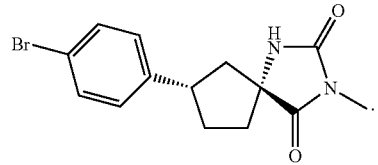

Formula 8

3. A process for the preparation of a compound of Formula 9

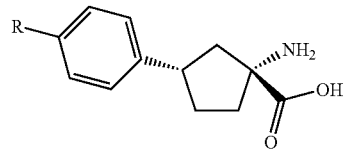

Formula 9 comprising the steps of hydrolizing Formula 8

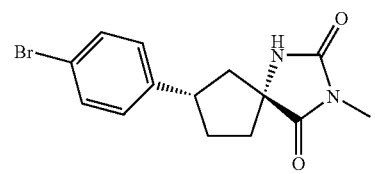

Formula 8 with an aqueous base to give a compound of Formula 9

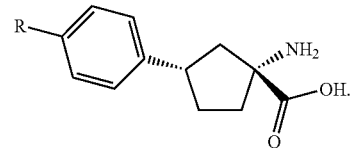

Formula 9

4. A process of isolating a compound of Formula 11a

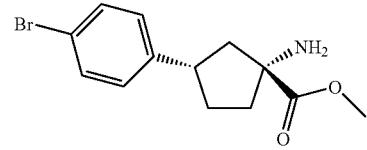

Formula 11a comprising the step of filtering the mixture of compounds of Formula 11a and Formula 11b

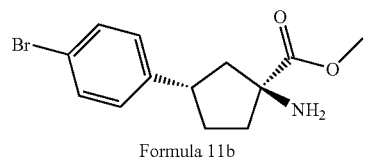

Formula 11a

+

Formula 11b to isolate a compound of Formula 11a

Formula 11a

* * * * *